United States Patent [19]
Hayashi et al.

[11] Patent Number: 5,495,849
[45] Date of Patent: Mar. 5, 1996

[54] BIOLOGIC MAGNETOMETER FOR DETERMINING AN ELECTRIC CURRENT DISTRIBUTION IN A LIVING ORGAN

[75] Inventors: Takehiko Hayashi; Takaki Shimura; Takao Goto; Yoshiyasu Nakashima, all of Kawasaki, Japan

[73] Assignee: Fujitsu Limited, Kawasaki, Japan

[21] Appl. No.: 268,675

[22] Filed: Jun. 30, 1994

Related U.S. Application Data

[63] Continuation of Ser. No. 924,484, Aug. 4, 1992, abandoned.

[30] Foreign Application Priority Data

Aug. 12, 1991 [JP] Japan .................................... 3-201028

[51] Int. Cl.$^6$ ...................................................... A61B 5/05
[52] U.S. Cl. ...................... 128/653.1; 324/244; 324/248; 364/577
[58] Field of Search ......................... 128/653.1; 324/244, 324/248, 260; 364/577, 413.02

[56] References Cited

U.S. PATENT DOCUMENTS

| | | | |
|---|---|---|---|
| 4,793,355 | 12/1988 | Crum et al. ........................... | 128/653.1 |
| 4,913,152 | 4/1990 | Ko et al. ............................... | 128/653.1 |
| 4,977,896 | 12/1990 | Robinson et al. ..................... | 128/653.1 |
| 5,170,119 | 12/1992 | Sekihara et al. ...................... | 128/653.1 |

OTHER PUBLICATIONS

Applied Optics, "Linear Estimation Theory Applied To The Reconstruction of a 3–D Vector Current Distribution", by Warren E. Smith, et al., vol. 29, No. 6, Feb. 10, 1990, pp. 658–669.

Academic Press, Second Edition, "Linear Algebra and Its Applications", by Gilbert Srang, pp. 136–145.

IEEE Transactions on Biomedical Engineering, vol. BME-34, *An Evaluation of Methods for Neuromagnetic Image Reconstruction*, Brian Jeffs et al., Sep. 1987, pp. 713–723.

*Advance in Biomagnetism*, Edited by Samuel J. Williamson et al., Plenum Press, New York, Aug. 13–18, 1989, pp. 149–156.

*Primary Examiner*—Ruth S. Smith
*Attorney, Agent, or Firm*—Staas & Halsey

[57] ABSTRACT

In a method/apparatus of the present invention, a plurality or pickup coils are employed at a plurality of detection points so as to measure magnetic field intensities induced from electric current generated on living organ: the detection points are spatially interpolated/extrapolated; equations to determine relations of a hypothetically located current to the magnetic field intensities at the detection points and the interpolated detection points are established; the magnetic field intensities are measured with the pickup coils; magnetic field intensities are estimated at the interpolated/extrapolated detection points from the magnetic field intensities measured by the pickup coils; and the hypothetically located electric current is calculated by applying said magnetic field intensities at the detection points and said interpolated/extrapolated detection points to said equation. Thus, the electric current value is estimated. The calculation is preferably carried out by a SVD method, where the hypothetically located current is placed at plural current source positions. Matrix constants in the SVD calculation is determined in advance to allow a quick calculation. The interpolated/extrapolated point may be determined according to a linear method or a spline method, or depending on the current location, or on the spatial differentiation of the magnetic field intensity, or may be changed with time.

9 Claims, 6 Drawing Sheets

FIG. 9(b)  $\left|\dfrac{\partial B(x)}{\partial x}\right|$

FIG. 10(b)
NO. OF INTERP.

TIME →

FIG. 10(c)
NO. OF INTERP.

TIME →

BIOLOGIC MAGNETOMETER FOR DETERMINING AN ELECTRIC CURRENT DISTRIBUTION IN A LIVING ORGAN

This application is a continuation of application Ser. No. 07/924,484, filed Aug. 4, 1992, now abandoned.

BACKGROUND OF THE INVENTION

1. Field of the invention

This invention relates to a biologic magnetometer for measuring electric currents biologically generated in a living organ so as to estimate position of active area of the living organ

2. Description of the Related Arts

In recent years the development of magnetometers employing superconductive quantum interface device, referred to hereinafter as a SQUID, has been allowing its wider applications in medical diagnosis apparatus.

In analyzing defects or mechanisms of human internal organs from the measured magnetic field intensities, the location of electric current source, which induces the magnetic field, must be necessarily determined. For this analysis an inverse problem must be solved. That is, the current source must be determined by being calculated from the measured magnetic field intensities. However, this calculation is extremely difficult because the matrix to present the relation between the currents and the magnetic field intensities is singular.

A first prior art procedure to estimate the current source location is hereinafter described. In estimating a current source of heart an infinite, homogeneous electrical conductor is hypothetically provided in the place of heart. For estimating a brain, a homogeneous sphere or cospherical multi-layer conductors are hypothetically provided in place of the brain. Next, a current source, which may be sometimes called a current dipole, is hypothetically provided on the hypothetically provided conductor. Next, magnetic field intensity generated by the current source is calculated according to Biot-Savart's law for each detection point where a plurality of pickup coils are respectively placed. Next, these calculated magnetic field intensities are compared with magnetic field intensities really measured with the pickup coils. Location and current amount of the hypothetical current source which provides the minimum difference, i.e. the least squares between the calculated magnetic field intensities and measured magnetic field intensities are searched; then it is determined as the current source. A first problem in this least squares method is in that in determining the current source a plurality of the hypothetical current source locations and a plurality of hypothetical current values thereof must be tried, consequently a considerably long time must be consumed because this try does not always result in converging the difference. There is also a second problem in that when the current sources are on plural locations the try (calculation) may lead to a similar but wrong solution called a local minimum, and of course it consumes a much longer time. Thus, it is practically impossible to obtain a unique solution or real time solution.

As a second prior art to avoid these problems, the long time consumption and the wrong solution, there is a method utilizing a singular value deposition, referred to hereinafter as SVD method. In the SVD method there are provided a plurality of pickup coils and a plurality of locations three-dimensionally placed current sources hypothetically provided, for example, on three-dimensionally configurated grids; and a simultaneous linear equation is determined according to Biot-Savart's law to present the relation between the currents and the magnetic field intensities at the pickup coils. After the equation based on the distances between the current sources and the coil locations is determined, the equation is fixed so that only the current values are tried to provide the least squares of the differences between the measured magnetic field intensities and the calculated magnetic field intensities, as well as provide the least total of the squares of the current values. In this method the current source distribution can be more quickly obtained than in the first prior art where the hypothetical current source locations are changed one by one, because the relation between the current values and the magnetic field intensities can be quickly given by using the already calculated inverse matrix of the simultaneous linear equations. This method was disclosed by Brian Jeffs, et al. on IEEE Transaction on Biomedical Engineering, vol. BME-34, No.9. September 1987.

Problem of the second prior art is in that in order to achieve a good resolution of the current source locations, the number m of the pickup coils is required to be equal to or larger than the number n of the three-dimensionally preset locations of the current sources. Accordingly, if the preset current source locations are on a several millimeter pitch on a 10 cm diameter heart, almost ten thousand of pickup coils are required together with their respective SQUID magnetometers. It is practically impossible to provide such a great number of pickup coils, as well as to provide an apparatus to display the heart movement in real time from the data measured by such a great number of the pickup coils.

SUMMARY OF THE INVENTION

It is a general object of the invention to provide a biological magnetometer achieving a good resolution of the current source locations while employing a small number of pickup coils so as to allow a real time display of the movement of the monitored object.

In a method/apparatus of the present invention to measure an electric current generated on a living organ, a plurality of pickup coils are employed at a plurality of detection points so as to measure magnetic field intensities induced from the electric current generated on the living organ: (a) the detection points are spatially interpolated/extrapolated; (b) equations to determine relations of a hypothetically located current to the magnetic field intensities at the detection points and the interpolated detection points (1M) are established; (c) the magnetic field intensities are measured with the pickup coils (1C); (d) magnetic field intensities are estimated at the interpolated/extrapolated detection points (1M) from the magnetic field intensities measured by the pickup coils (1C); and (e) the hypothetically located electric current is calculated by applying the magnetic field intensities at the detection points (1A) and the interpolated/extrapolated detection points (1M) to said equation. Thus, the electric current value is estimated. The calculation is preferably carried out by a singular value decomposition (SVD) method, where the hypothetically located current is placed at plural current source positions. Matrix used as constants in the SVD calculation is determined in advance so as to allow a quick calculation. The interpolated/extrapolated point may be determined according to a linear method or a spline method, or depending on the location of the current, or on the spatial differentiation of the measured magnetic field intensity, or may be changed with time.

The above-mentioned features and advantages of the present invention, together with other objects and advantages, which will become apparent, will be more fully described hereinafter, with references being made to the accompanying drawings which form a part hereof, wherein like numerals refer to like parts throughout.

DESCRIPTION OF THE PREFERRED EMBODIMENT

Figure 1:
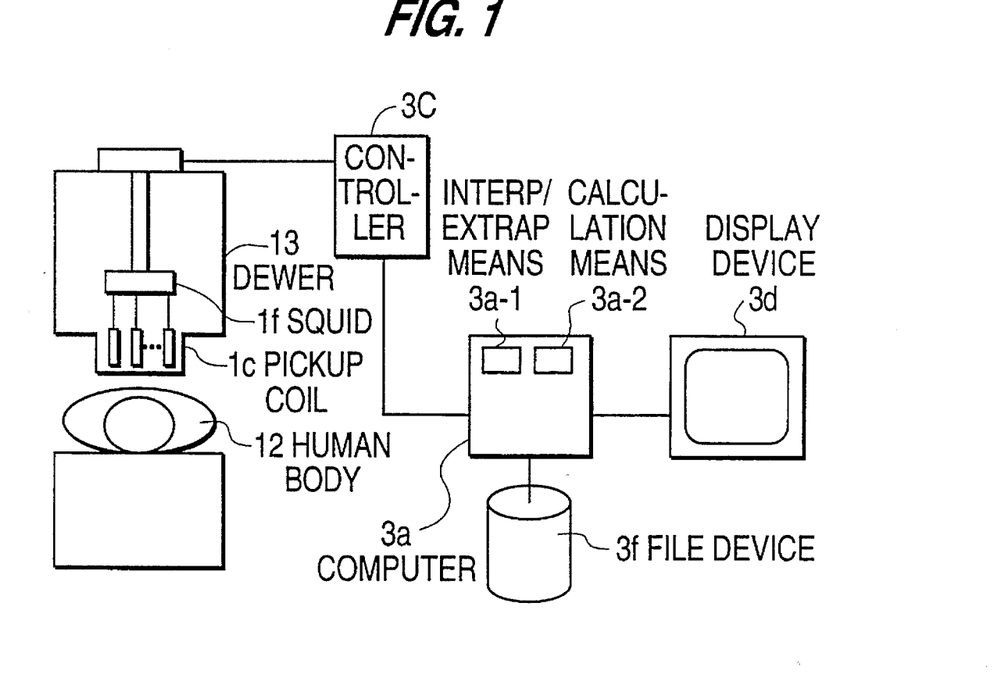
FIG. 1 schematically illustrates a configuration of the biologic magnetometer where the present invention is embodied.

Referring to FIG. 1 to FIG. 6, the preferred embodiment of the present invention is hereinafter described. FIG. 1 schematically illustrates a biological magnetometer apparatus where the present invention is embodied. Pickup coils $1c$ are located over the object, such as a heart, to be monitored of a human body 12. The pickup coils $1c$ measure magnetic field intensities induced by biological currents generated on the heart. The signals picked up by the pickup coils 1C are respectively detected by SQUID magnetometers $1f$ cooled in a dewer 13. A controller 3C controls the SQUID magnetometers to properly operate. A computer $3a$ receiving the data output from SQUID magnetometers $1f$ processes the input data so as to find the current sources, i.e. current values on the preset locations. Details of the processings, i.e. calculations, are described later in detail. The calculated current values are displayed on a display screen $3d$. A file device $3f$ stores programs necessary for the operation of computer $3c$ and thus obtained data for the apparatus of an MRI (magnetic resonance imaging) or an X-ray CT (computer tomography).

Figure 2:
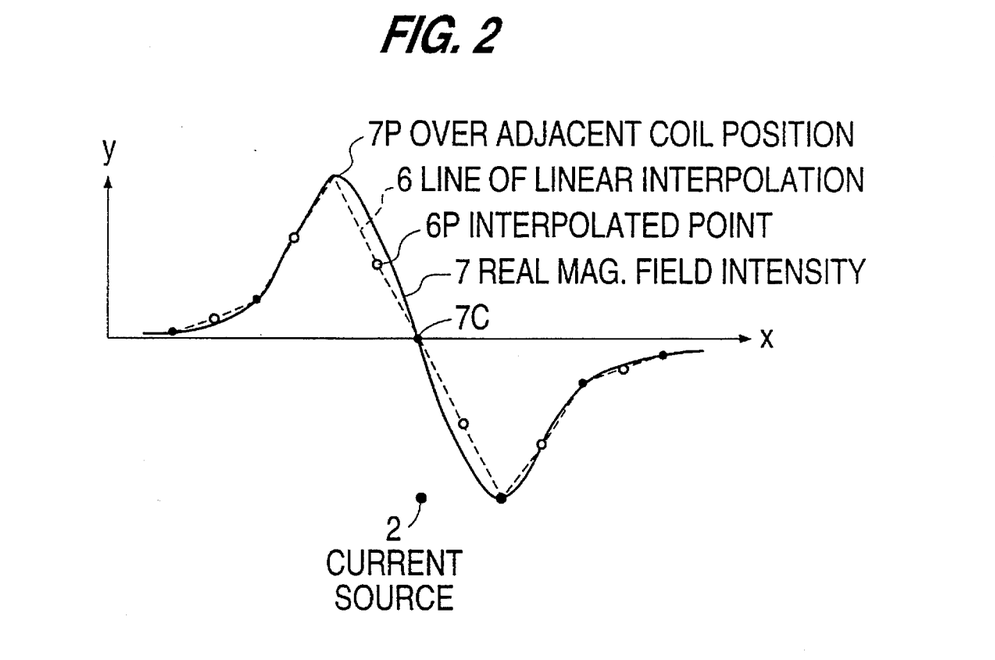
FIG. 2 shows a magnetic field intensity induced from a single current source measured by a single pickup coil when the location of the current source is horizontally FIG. 3 schematically illustrates a prior art grid on which current sources are located and a grid on which pickup coils are located.

As a preparation of the apparatus of the present invention, detection characteristics of the pickup coil is measured. In FIG. 2 there is plotted a solid curve 7 showing the detected magnetic field intensity on the Y ordinate when a pickup coil whose axis is directed towards a current source 2 is shifted along X abscissa orthogonally from the coil axis. The curve 7 varies depending on the distance from the current source.

Figure 3:
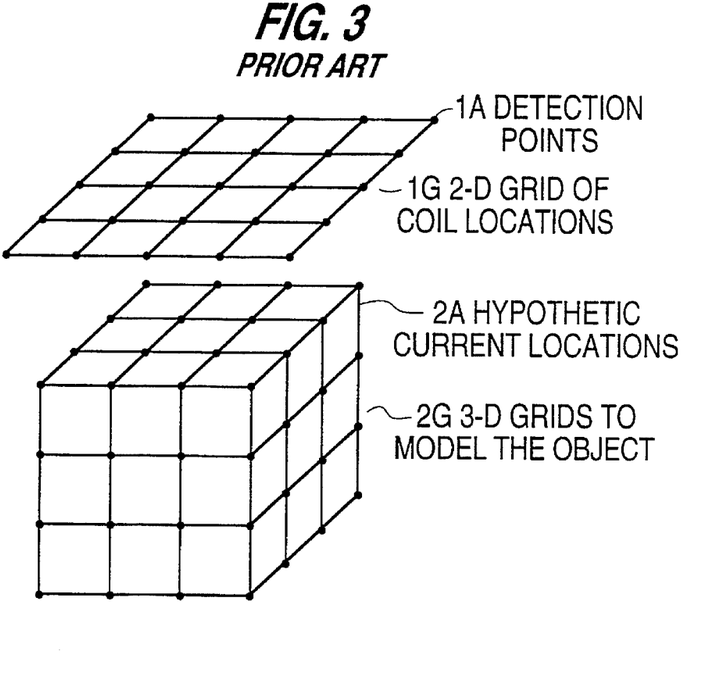

On the other hand, three-dimensional grids 2G are assumed in the place of the object to be observed as shown in FIG. 3. Pitch of the grids is, for example 3 to 5 mm. Black dots 2A indicate locations of hypothetical current sources (step 1 of FIG. 5). Though in FIG. 3 black dots are not drawn inside the cube of grids 2G there exist of course black dots inside the cube. Though the three-dimensional grids are drawn cubic the shape is arbitrarily chosen so as to properly represent the heart.

Another grid 1G typically of 20 to 30 mm pitch is two-dimensionally configured over grid 2G so as to indicate locations of the axes of pickup coils 1C. Explanation is now made with a single pickup coil at a single detection point for simple explanation; however, there may be provided three coils to detect three-dimensional magnetic field intensity, i.e. a vector of the magnetic field intensity, at the single detection point. Moreover, in practical cases the coils may often be arranged on a spherical grid; however, the two-dimensional arrangement is now referred to for the sake of simple explanation.

Figure 4:
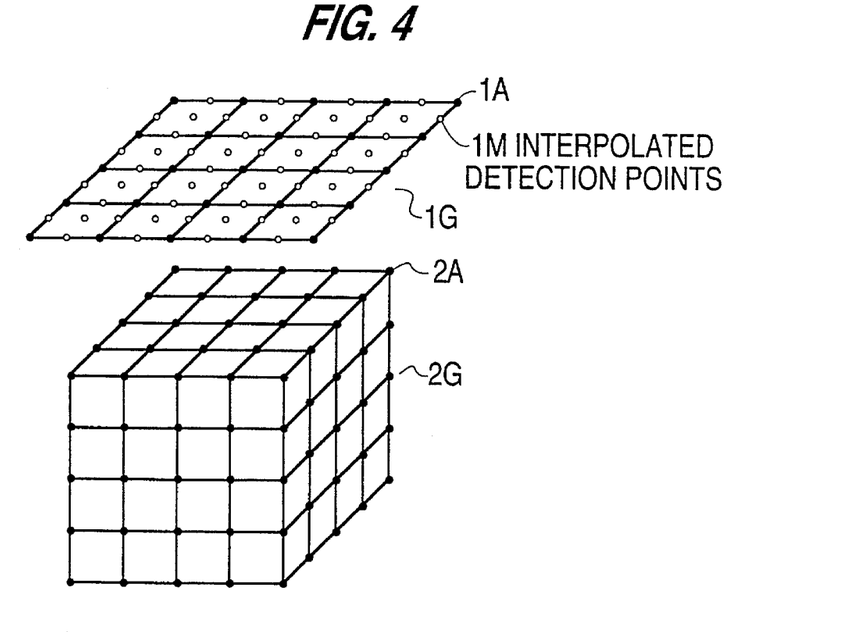
FIG. 4 schematically illustrates the first preferred embodiment of the present invention.
Figure 5:
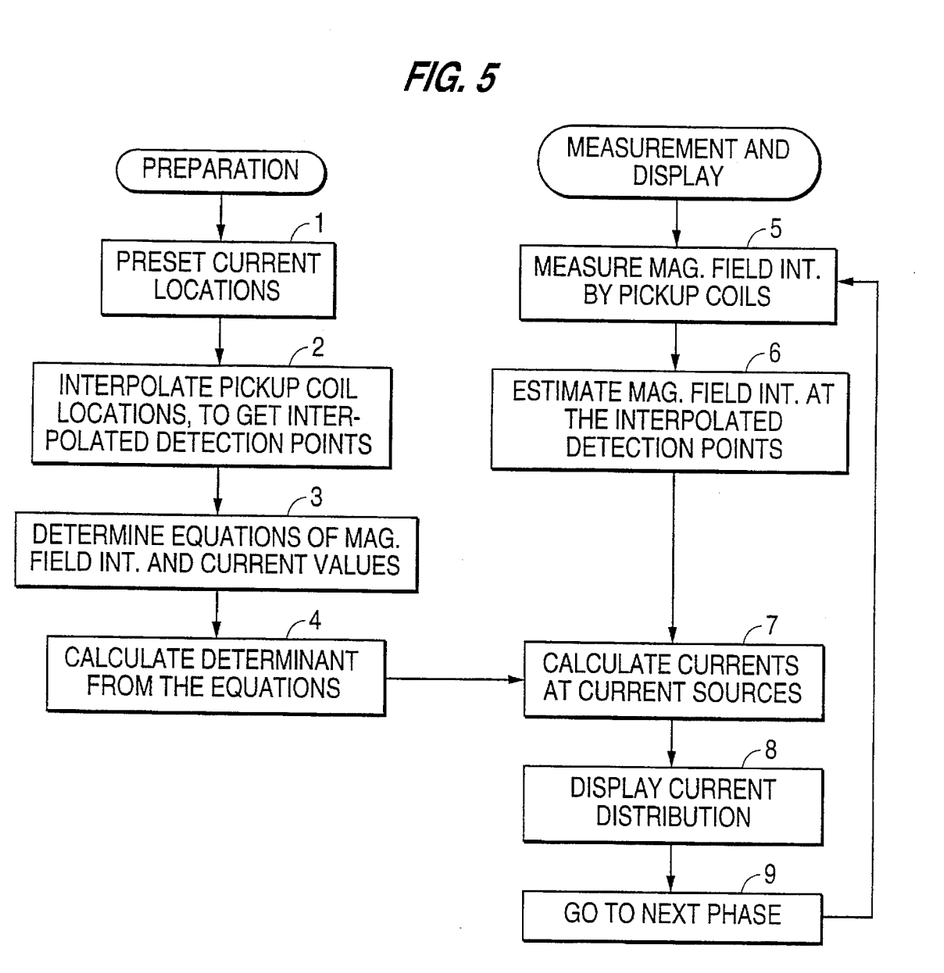
FIG. 5 is a flow chart showing the steps of the first preferred embodiment of the present invention.

Next, the detection points 1A of the pickup are interpolated as indicated with white dots 1M in FIG. 4 where the interpolation is by a hair of the grid pitch (step 2). The white dots are hereinafter called as interpolated detection points.

Next, simultaneous linear equations (1) to define the relation of the current values and the magnetic field intensities at the real/interpolated detection points are established according to Biot-Savart's law as described later, where the equations are based on the distances between each of the hypothetical current sources and each or the locations of the real/interpolated detection points. (step 3)

Inverse matrix usable as coefficients to calculate current values from the measured/interpolated magnetic field intensities, referred to later as $A^+$, is calculated. (step 4)

The calculations to obtain current values from the measured magnetic field intensities are hereinafter described in detail. Vectors of currents located respectively at n current source locations $(x_1', y_1', z_1'), \ldots (x_n', y_n', z_n')$ are given as $(q_{1x}, q_{1y}, q_{1z}), \ldots (q_{nx}, q_{ny}, q_{nz})$. Magnetic field intensities measure by m pickup coils located respectively at $(s_1, y_1, z_1), \ldots (x_n, y_n, z_n)$ are given as $(b_{1x}', b_{1y}', b_{1y}', b_{1z}'), \ldots (b_{mx}', b_{my}', b_{mz}')$, where the magnetic field intensities are given as vector values.

Then, magnetic field intensities $b_1 \ldots b_m$ are given by equation (1), according to Biot-Savart's law, as $$\begin{bmatrix} b_1 \\ b_2 \\ \cdot \\ \cdot \\ b_m \end{bmatrix} = \begin{bmatrix} a_{11} & a_{12} & \cdot & \cdot & a_{1n} \\ a_{21} & a_{22} & \cdot & \cdot & a_{2n} \\ \cdot & & a_{ij} & \cdot & \cdot \\ \cdot & & & & \\ a_{m1} & a_{m2} & \cdot & \cdot & a_{mn} \end{bmatrix} X = \begin{bmatrix} q_{1n} \\ q_2 \\ \cdot \\ \cdot \\ q_n \end{bmatrix} \quad (1)$$

where, $$a_{ij} = \frac{\mu_o}{4\pi\{(x_i - x_j')^2 + (y_i - y_j')^2 + (z_i - z_j')^2\}^{3/2}}$$

$$x \begin{vmatrix} 0 & z_i - z_j' & -(y_i - y_j') \\ -(z_i - z_j') & 0 & x_i - x_j' \\ y_i - y_j' & -(x_i - y_j') & 0 \end{vmatrix} \quad (2)$$

where $\mu_o$ is permeability of vacuum.

Accordingly, it is given that:

$$B = AQ \quad (3)$$

where $$B = \{b_1, b_2, \ldots b_m\}^t \quad (4)$$

$$A = \begin{bmatrix} a_{11} & a_{12} & . & . & a_{1n} \\ a_{21} & s_{22} & . & . & a_{2n} \\ . & . & & . & . \\ . & . & & . & . \\ a_{m1} & a_{m2} & . & . & a_{mn} \end{bmatrix} \quad (5)$$

$$Q = \{q_1, q_2, \ldots q_m\}^T \quad (6)$$

Thus, the equation (3) being a linear equation seems to be solvable so as to obtain the current distribution Q. However, it is impossible to find a unique solution from matrix A because each of the rows is not independent, in other words the rows have some dependency.

Therefore, in order to obtain the solution there is employed the SVD method. The SVD method is to search a condition such that the difference between actually measured magnetic field intensities $B_m$ and magnetic field intensities B calculated from hypothetically provided current values Q on each current source location indicated with the black dots by means of the least squares method, as well as the total of squares of the current values, $\Sigma Q_i^2$, becomes minimum.

A practical method to obtain the solution of the SVD is hereinafter described in detail. The below-described calculations are disclosed also in the reference cited in the above Description of Related Arts.

Matrix A can be decomposed to the factors as:

$$A = U\Sigma V^T \quad (7)$$

where U and V are orthogonal matrices of given vectors corresponding to given values of $AA^T$ and $A^TA$, respectively, and $\Sigma$ is a diagonal matrix whose elements are called singular values derived from given values of $AA^T$ or $A^TA$ aligned in the descendent order.

Then, solution of the least squares of equation (3) is derived as follows:

$$Q^+ = V^T \Sigma + UB_m = A + B_m \quad (8)$$

where $$\Sigma = \begin{vmatrix} \sigma_1 & & 0 \\ & \ldots & \\ 0 & & \sigma_r \end{vmatrix} \quad (9)$$

$$\Sigma^+ = \begin{vmatrix} 1/\sigma_1 & & 0 \\ & \ldots & \\ 0 & & 1/\sigma_r \end{vmatrix} \quad (10)$$

where $\sigma_1$ are singular values of A, and their suffix r indicates the rank of matrix A. (step 4)

Finally, $A^+$ is obtained as follows:

$$A^+ = V\Sigma + V^T \quad (11)$$

Thus, the preparation of the measurement is now completed. Once the value of $A^+$ is calculated, i.e. determined, the calculation of equation (8), i.e. the reverse calculation, can be simply and quickly done by once-multiplying a matrix by a vector, where the calculated result can be used as a constant in later calculations of measured data.

A procedure to monitor the object is hereinafter described. First, the magnetic field intensities are measured with the pickup coils. (step 5)

Next, magnetic field intensities at the interpolated detection points 1M, referred to hereinafter as interpolated magnetic field intensities, are estimated by computer 3a from the magnetic field intensities really measured by pickup coils according to the already prepared data shown in FIG. 2. (step 6)

The simplest method of estimating the magnetic field intensities at the interpolated detection points is a linear interpolation, where the magnetic field intensity is estimated by dotted straight line 6 which connects the two magnetic field intensities 7C and 7P respectively at the present coils and the adjacent coils as shown in FIG. 2, where black dots indicate the magnetic field intensities measured by pickup coils, and white dots 6P indicate the magnetic field intensities to be given to the interpolated detection points. Other methods or estimation for the interpolated detection points will be described later.

Next, currents on the three-dimensional grids are calculated from both the really measured magnetic field intensities and the interpolated magnetic field intensities according to equation (8) employing the already-determined value of matrix $A^+$ as a constant. (step 7)

Next, thus obtained current density distribution on the object is displayed on display device 3d. (step 8)

Now the measurement routine for a single phase is completed, and the procedure goes back to step 5 for the next phase (step 9) so that the real time monitoring of an acting object is accomplished.

Figure 6:
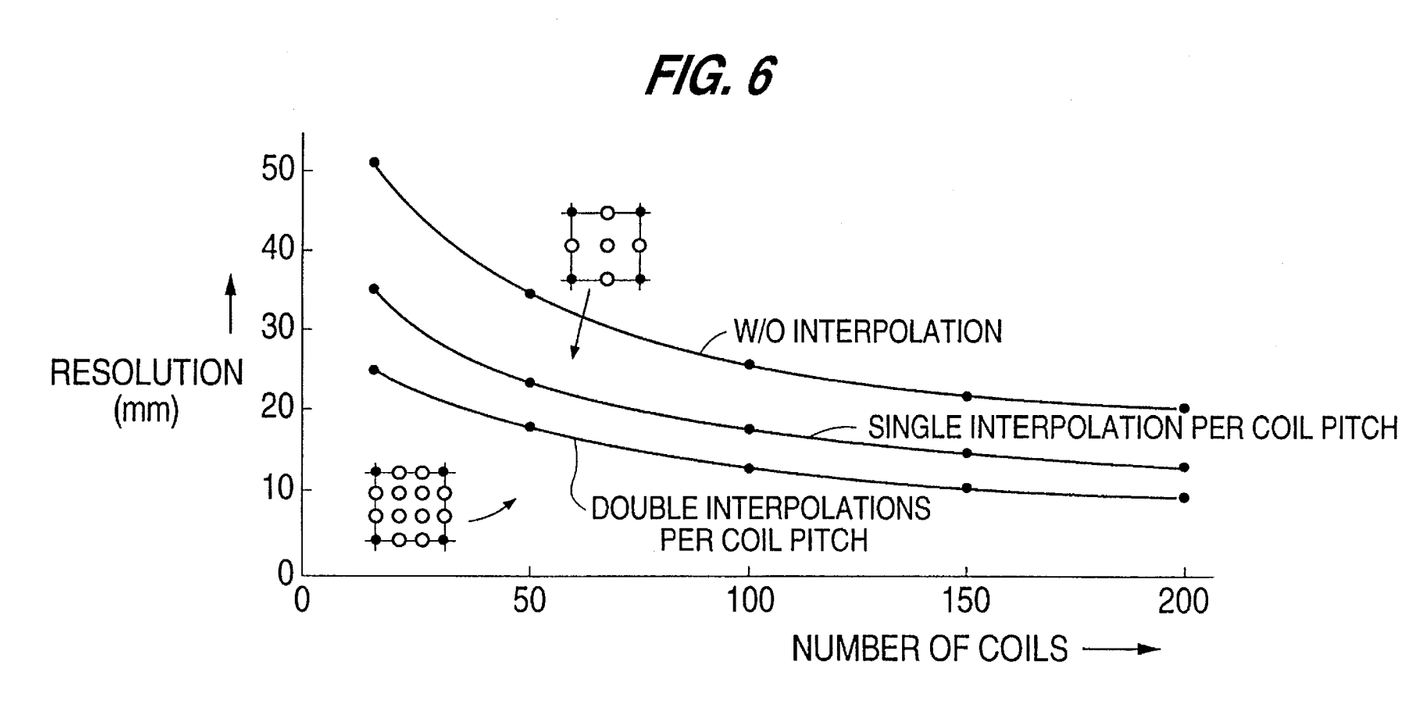
FIG. 6 shows the effect of the interpolated points.

Thus great number of the magnetic field intensity data enhanced by the interpolation/extrapolation improves the resolution of the current density distribution. The most typical practice the present inventor had is such that the number of the assumed current sources is 150 and the number of pickup coils is also 150. With these conditions it is seen in FIG. 6 that the resolution is doubled by the two interpolations in a single grid pitch.

Figure 7:
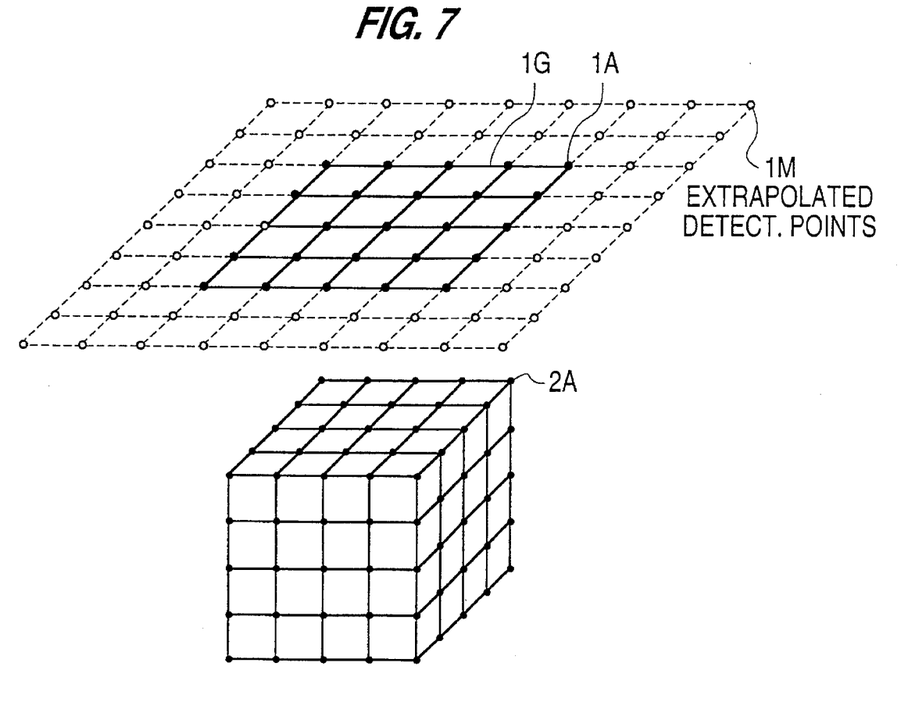
FIG. 7 schematically illustrates the second preferred embodiment of the present invention.

Instead of the interpolation of the first preferred embodiment the pickup coils are extrapolated in the second preferred embodiment as shown with white dots 1M in FIG. 7. Here is also the same advantageous effect that the resolution is improved.

Figure 8:
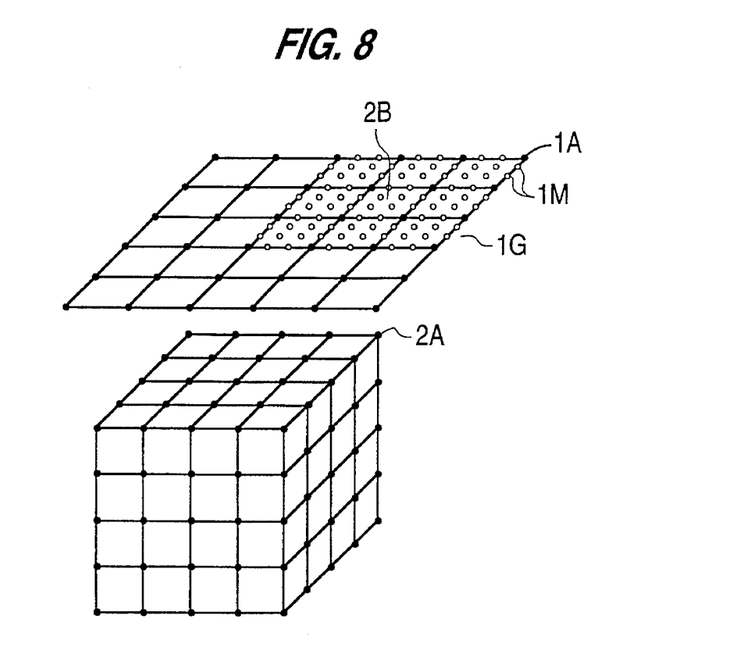
FIG. 8 schematically illustrates the third preferred embodiment of the present invention.

In the third preferred embodiment in stead of the uniform interpolation of the first preferred embodiment the pickup coils are interpolated particularly in the area in the vicinity of the current sources as shown with white dots 1M in FIG. 8, where the arrow 2B is drawn exactly above the current source. The advantageous effect is in that the improved resolution is accomplished with the minimum increase in the number of the pickup coils.

In estimating the interpolated magnetic field intensities, the linear estimation of FIG. 2 may be replaced with a higher order function, such as the second order or the third order, or a spline function. The advantageous effect is in that the current source can be more accurately located though the calculation takes more time.

Figures 9A, 9B:
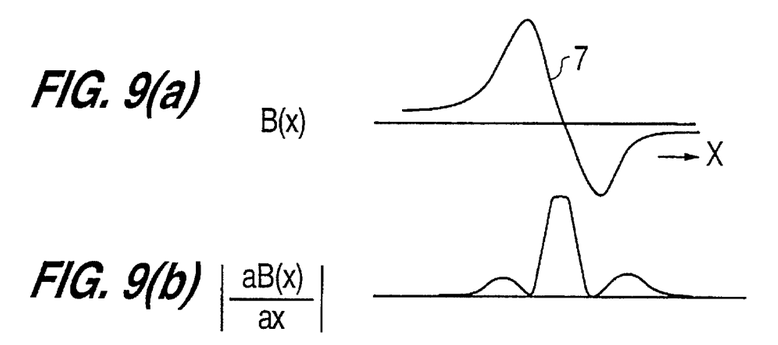
FIG. 9 shows interpolation depending on the spatial differentiation of the magnetic field intensity.
Figure 9C:
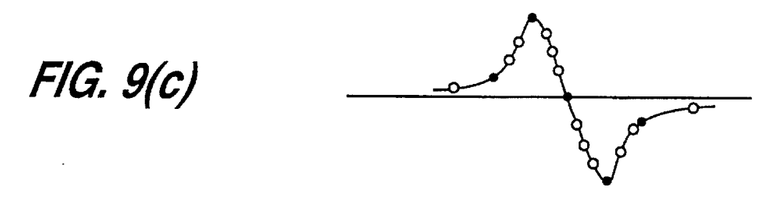

Though in the first and second preferred embodiments the interpolated detection points are separated from the adjacent ones by a uniform pitch the interpolated detection points may be located particularly at a place where the change in the magnetic field intensity is great, that is, the place where the spatial differentiation of the magnetic field intensity curve (solid curve) 7 of FIG. 2 and FIG. 9(a) is great, as shown with white dots in FIG. 9(c). FIG. 9(b) shows a spatial differentiation of the FIG. 9(a) curve. This method efficiently provides the interpolated detection points of the pickup coils.

Figure 10A:
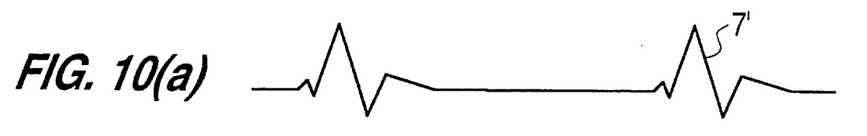
FIG. 10 shows the number of interpolation/extrapolation depending on the change in the magnetic field intensity with time.
Figure 10B:
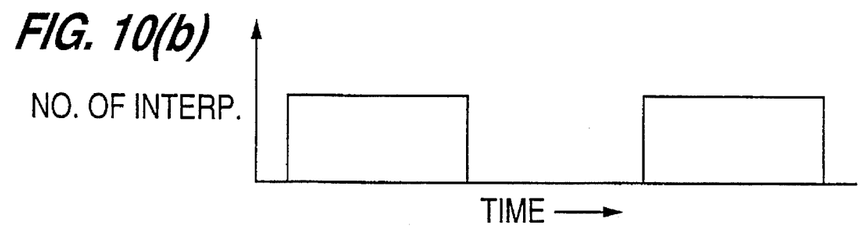
Figure 10C:
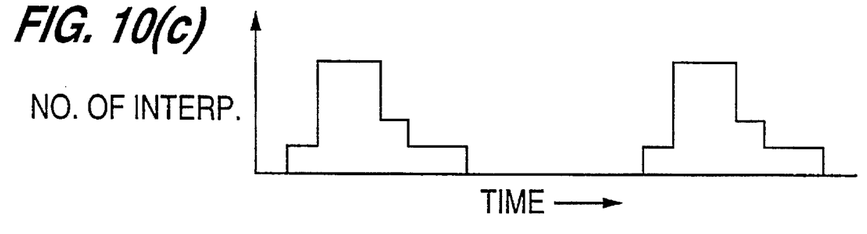

In monitoring an object whose motion changes with time, such as the heart, shown with magnetic field intensity curve 7' in FIG. 10(a), the interpolated detection point itself or the number of the interpolated detection point may be determined depending on the amount of the differentiation of FIG. 10(*a*) curve by time as shown in FIG. 10(*b*) and FIG. 10(*c*), respectively. In other words, the interpolation is carried out only when the heart generates the currents, and the number of the interpolation is increased only on the change in the generated currents. The not-always-carried-out interpolation relaxes the load of the computer resulting in efficiently locating the current sources.

Though in the above preferred embodiments the calculation of the currents is carried out according to the SVD method, it is apparent that the concept of the present invention that the detection points with pickup coils are interpolated/extrapolated can be applied to any other type or calculations.

Though in the above preferred embodiments the object to be monitored is referred to as human heart or brain, it is apparent that the method/apparatus of the present invention can be embodied for other objects than the heart or brain, as well as other than human.

The above-described interpolation/extrapolation estimation, calculation of the constants, calculation of the currents, etc. and operation of display device 3*d* are carried out by computer 3*a* having respective programs installed therein.

The many features and advantages of the invention are apparent from the detailed specification and thus, it is intended by the appended claims to cover all such features and advantages of the methods which fall within the true spirit and scope of the invention. Further, since numerous modifications and changes will readily occur to those skilled in the art, it is not detailed to limit the invention and accordingly, all suitable modifications are equivalents may be resorted to, falling within the scope of the invention.

What we claim is:

1. A biologic magnetometer for measuring an electric current generated on a living organ, comprising:

a plurality of pickup coils for measuring magnetic field intensities induced from the current;

interpolation and extrapolation means for one of spatially interpolating locations and extrapolating locations of the pickup coils so as to determine one of an interpolation point and extrapolation point, and estimating magnetic field intensities at said one of interpolation point and extrapolation point from said magnetic field intensities measured by said pickup coils; and calculation means for calculating an amount and a location of a hypothetically located electric current by the use of both said magnetic field intensities measured by said pickup coils and said magnetic filed intensities estimated at said one of interpolated point and extrapolated point, wherein the electric current is determined and the calculation means includes a computing device.

2. A biologic magnetometer as recited in claim 1, further comprising means for displaying said amount and location of the current.

3. A biologic magnetometer as recited in claim 1, wherein said interpolation and said extrapolation means operates one of a linear interpolation and a linear extrapolation.

4. A biologic magnetometer as recited in claim 1, wherein said interpolation and extrapolation means operates a spline interpolation.

5. A biologic magnetometer as recited in claim 1, wherein said interpolation and extrapolation means determines one of said interpolated point and extrapolated point depending on location of the electric current.

6. A biologic magnetometer as recited in claim 1, wherein said interpolation and extrapolation means determines said one of interpolation point and extrapolation point at a place where a spatial differentiation of the magnetic field intensities detected by the pickup coil is great.

7. A biologic magnetometer as recited in claim 1, wherein said interpolation and extrapolation means determines said interpolated/extrapolated point depending on a proportion to a spatial differentiation of said magnetic field intensity measured by the pickup coil.

8. A biologic magnetometer as recited in claim 1, wherein said interpolation and extrapolation means changes said one of interpolation point and extrapolation point with time depending on a proportion to a spatial differentiation of said magnetic field intensity measured by the pickup coil.

9. A biologic magnetometer as recited in claim 1, wherein said calculation is carried out according to a singular value decomposition method, where a constant is determined in relation between the magnetic field intensity detected by the pickup coil and the current in advance so that said constant is used in said calculation.

* * * * *

UNITED STATES PATENT AND TRADEMARK OFFICE
CERTIFICATE OF CORRECTION

PATENT NO. : 5,495,849

DATED : March 5, 1996

INVENTOR(S) : Takehiko HAYASHI et al.

It is certified that error appears in the above-indentified patent and that said Letters Patent is hereby corrected as shown below:

On the title page, item [57], line 1, change "or" to --of--.

Col. 3, line 15, after "horizontally" insert --;--.

Col. 4, line 29, change "or" to --of--;
line 39, change "$(s_1,$" to --$(x_1,$--;
line 67, change "$b_m\}'$" to --$b_m\}^T$--.

Col. 6, line 39, change "in stead" to --instead--.

Col. 8, line 4, "change "filed" to --field--.

Signed and Sealed this

Fourth Day of June, 1996

Attest:

BRUCE LEHMAN

Attesting Officer

Commissioner of Patents and Trademarks